(12) United States Patent
Madhra et al.

(10) Patent No.: US 8,093,426 B2
(45) Date of Patent: Jan. 10, 2012

(54) INTERMEDIATE COMPOUNDS AND THEIR USE IN PREPARATION OF LACOSAMIDE

(75) Inventors: Mukesh Kumar Madhra, Karnal (IN); Pankaj Kumar Singh, Kanpur (IN); Chandra Has Khanduri, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 483 days.

(21) Appl. No.: 12/327,124

(22) Filed: Dec. 3, 2008

(65) Prior Publication Data

US 2009/0143472 A1    Jun. 4, 2009

(30) Foreign Application Priority Data

Dec. 4, 2007    (IN) .......................... 2542/DEL/2007

(51) Int. Cl.
C07C 233/65 (2006.01)
(52) U.S. Cl. ........ 564/165; 564/164; 562/441; 514/567; 514/620
(58) Field of Classification Search .................. 564/164, 564/165; 562/441; 514/567, 620
See application file for complete search history.

(56) References Cited

U.S. PATENT DOCUMENTS

RE38,551 E    7/2004 Kohn ............................ 514/616

FOREIGN PATENT DOCUMENTS

| EP | 0 613 883 | 9/1994 |
| WO | WO9733861 | * 9/1997 |
| WO | WO 00/00463 | 1/2000 |
| WO | WO 2006/037574 | 4/2006 |

OTHER PUBLICATIONS

Anderson et al., "A Reinvestigation of the Mixed Carbonic Anhydride Method of Peptide Synthesis", *Journal of the American Chemical Society*, 89(19):5012-5017 (1967).
Morieux et al., "Synthesis and anticonvulsant activities of N-benzyl(2R)-2-acetamido-3-oxysubstituted propionamide derivatives", *Bioorganic & Medicinal Chemistry*, 16(19):8968-8975 (2008).
Andurkar et al., "Synthesis and anticonvulsant activities of (R)-(0)-methylserine derivatives", *Tetrahedron: Asymmetry*, 9(21):3841-3854 (1998).
Barlos et al., "Convenient Synthesis of N-Trityl-O-Alkyl-L-Hydroxyamino Acids and Derivatives", *Tetrahedron*, 39(3):475-478 (1983).
Sowinski and Toogood, "Synthesis of an Enantiomerically Pure Serine-Derived Thiazole", *Journal of Organic Chemistry*, 61(22):7671-7676 (1996).
Sheehan et al., "Activated Cyclic Derivatives of Amino Acids", *Journal of the American Chemical Society*, 81:6086 (1959).
Ide et al., "Conjugation of Selenols with Aziridine-2-Carboxylic Acid-Containing Peptides", *Synlett*, 13:2011-2014 (2005).

* cited by examiner

*Primary Examiner* — Shailendra Kumar

(57) ABSTRACT

The present invention is concerned with novel compounds and their use for the preparation of lacosamide. The present invention also contemplates processes for the preparation of lacosamide employing the novel compound of general Formula II, Formula IIa or Formula IIb as intermediate.

Formula II

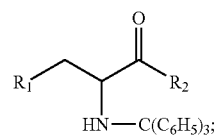

Formula IIa

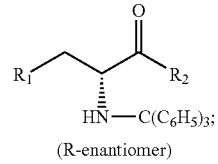

(R-enantiomer)

Formula IIb

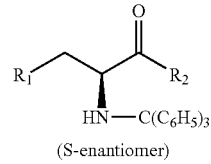

(S-enantiomer)

Wherein
$R_1$ is —OH or —OMe;
$R_2$ is —OH or —NH—CH$_2$—C$_6$H$_5$.

1 Claim, No Drawings

INTERMEDIATE COMPOUNDS AND THEIR USE IN PREPARATION OF LACOSAMIDE

FIELD OF THE INVENTION

The present invention relates to intermediate compounds and their use in preparation of lacosamide.

BACKGROUND OF THE INVENTION

Lacosamide (SPM 927, also referred to as harkoseride or ADD 234037), is chemically (R)-2-acetamido-N-benzyl-3-methoxypropionamide of Formula Ia. It shows effects in the treatment of pain, epilepsy, fibromyalgia syndrome, osteoarthritis and migraine. It is also known to be useful for the treatment of CNS disorders in humans.

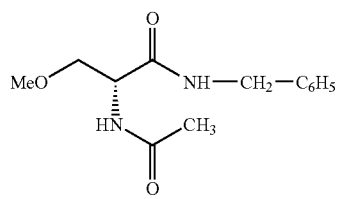

Formula Ia

Lacosamide and its methods of preparation are disclosed in U.S. Reissue Pat. No. RE 38,551 (hereinafter referred to as the '551 patent). This reference provides three general methods for the preparation of lacosamide. The first two methods do not involve the protection of active groups in intermediate compounds (such as amino, hydroxy and carboxylic acid groups). The other method disclosed in the '551 patent involves protection of an amino group present in D-serine with carbobenzoxy chloride (Cbz-Cl), subsequent O-methylation at the hydroxy group followed by benzylamination at carboxylic (—COOH) group and finally removal of the 'Cbz' group followed by acetylation produces lacosamide.

An alternative method for the preparation of lacosamide is disclosed in PCT publication WO 2006/037574 (hereinafter referred to as '574 application) that involves O-methylation of N-Boc-protected-D-serine ("Boc" refers to t-butoxycarbonyl) directly in one step by avoiding simultaneous formation of the methyl ester moiety.

In view of the preparation methods available for lacosamide, there is a need for simple and cost effective processes for the preparation of lacosamide that eliminates racemization of intermediate compounds and final product and provides improved efficiency per reaction volume in terms of yield, purity and chiral purity.

SUMMARY OF THE INVENTION

A new method for the preparation of lacosamide that gives excellent chiral purity and yield at low cost is provided. The new method involves the use of particular intermediate compounds. The intermediate compounds of the present invention comprise bulky protecting groups that are capable of minimizing nucleophilic attack at chiral carbon atom, which is otherwise responsible for racemization, providing the chirally pure lacosamide in high yield.

The present invention makes use of a bulkier group than "Boc" and "Cbz" during the present invention.

Thus, the novel intermediate compounds and use thereof for the preparation of lacosamide are aspects of the present invention.

Accordingly, the present invention is directed to compound of Formula II

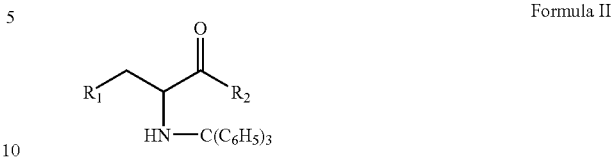

Formula II wherein
R$_1$ is —OH or —OMe;
R$_2$ is —OH or —NH—CH$_2$—C$_6$H$_5$ and the pharmaceutically acceptable salts, solvates, hydrates or enantiomeric forms thereof.

The compound of Formula II is useful pharmaceutical intermediate for the preparation of lacosamide.

The present invention also contemplates processes for the preparation of lacosamide employing the compound of Formula II as an intermediate.

The present invention also provides lacosamide substantially free of (S)-2-acetamido-N-benzyl-3-methoxypropionamide.

DETAILED DESCRIPTION OF THE INVENTION

The term "lacosamide" as used herein refers to the R-enantiomeric form of 2-acetamido-N-benzyl-3-methoxypropionamide.

The term "O-methylation" as used herein refers to attachment of a methyl group to the main chain of a given compound through an oxygen bridge. Alternatively the "O-methylation" is a process of converting an —OH group into an —OMe group in a given chemical compound. The term "benzylamination" as used herein refers to attaching an —NH—CH$_2$—C$_6$H$_5$ group in a given compound in such a way that the terminal —NH moiety can form an amide group. The term "de-tritylation" as used herein refers to removal of a trityl group from a given compound. The term "acetylation" as used herein refers to attachment of a —COMe group to the N$^2$-amino group of a given compound. The term "N$^2$-amino" refers to the amino group located at the second position in the main carbon chain of a given compound. The term "trityl" as used herein refers to a triphenylmethyl group and "Me" refers to a methyl group.

The term "alkoxy" as used herein refers to an —O-alkyl group, wherein the alkyl group has C$_1$-C$_6$ carbon atoms such as methyl, ethyl, propyl, butyl, isobutyl, isopropyl, t-butyl, etc.

In a first aspect, a compound of the general Formula II is provided,

Formula II wherein R$_1$ is —OH or —OMe; and R$_2$ is —OH or —NH—CH$_2$—C$_6$H$_5$ and pharmaceutically acceptable salt, solvate, hydrate or enantiomeric form thereof.

In an embodiment of this aspect, the compound of Formula II can exist independently as the R-enantiomer (Formula IIa), S-enantiomer (Formula IIb) or mixture.

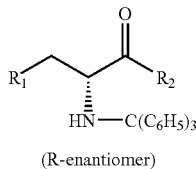

Formula IIa (R-enantiomer)

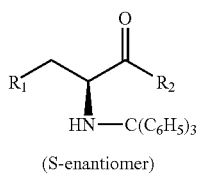

Formula IIb (S-enantiomer)

In another embodiment of the present aspect, the $R_1$ and $R_2$ are —OH.

In another embodiment of the present aspect, the $R_1$ is —OH and $R_2$ is —NH—CH$_2$—C$_6$H$_5$.

In another embodiment of the present aspect, the $R_1$ is —OMe and $R_2$ is —OH.

In another embodiment of the present aspect, the $R_1$ is —OMe and $R_2$ is —NH—CH$_2$—C$_6$H$_5$.

In another embodiment of the present aspect, the compound of Formula II is N-trityl-D-serine; O-methyl-N-trityl-D-serine; N-benzyl-O-methyl-N²-trityl-D-serinamide or N-benzyl-N²-trityl-D-serinamide.

The compound disclosed herein should be substantially pure, i.e., substantially free from impurities. For example, the compound can be about 85% pure (w/w), or, for example, greater than about 90% pure (w/w), or, for example, than about 99% pure (w/w).

In another embodiment of this aspect, the compounds presented herein can be enantiomerically pure, e.g., at least about 98% enantiomerically pure. One enantiomer substantially free of other enantiomer can be prepared. One enantiomer having no detectable amount of other enantiomer is another aspect of this disclosure.

The present aspect also contemplates use of compound of Formula II, Formula IIa or Formula IIb for the preparation of lacosamide.

In a second aspect, a process for the preparation of 2-acetamido-N-benzyl-3-methoxypropionamide of Formula I is provided.

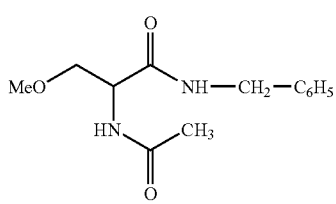

Formula I comprising the steps of:
a) O-methylating the compound of Formula III

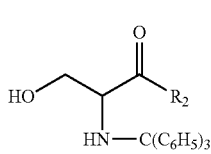

Formula III to produce a compound of Formula IV

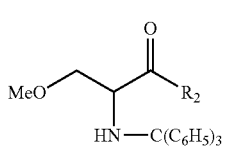

Formula IV wherein $R_2$ is —OH or —NH—CH$_2$—C$_6$H$_5$;
b) optionally benzylaminating the compound of Formula IV to produce a compound of Formula V;

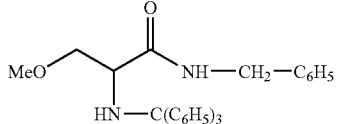

Formula V c) de-tritylating the compound of Formula V to produce the compound of Formula VI;

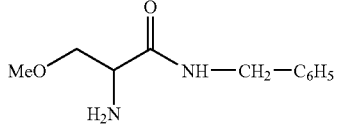

Formula VI d) acetylating the compound of Formula VI to produce the compound of Formula I.

In an embodiment of this aspect, the O-methylation step a) is performed by means of a methylating agent. Methylating agents such as methyl iodide, dimethyl sulfate, trimethyl silyldiazomethane, dimethyl sulfoxide (DMSO), for example, can be used for this purpose. The O-methylation can be performed, under, for example, Williamson conditions by treating the compound of Formula III with QX, wherein Q is alkoxy and X is a leaving group, such as, for example, the tosyl (p-toluenesulfonyl) or mesyl (methanesulfonyl) group. The O-methylation can also be performed either by using an organometallic compound with the methylating agent or by a phase-transfer reaction, for example, as described in PCT application WO 2006/37574. The O-methylation is generally performed in the presence of a base. The base can be, for example, hydride, hydroxide and/or oxides of metals, for example, hydride, hydroxide and/or oxides of sodium, potassium, calcium, silver, etc. can be used as base. The O-methylation can optionally be performed in the presence of a catalyst. Compounds including for example, imidazole, dimethylaminopyridine (DMAP), pyridine etc. can be used as catalysts in the reaction. The solvents that can be used for the O-methylation reaction are generally organic solvents. For example, polar organic solvents, e.g., tetrahydrofuran (THF), dimethyl sulfoxide (DMSO), acetonitrile (MeCN) etc. can be used.

Accordingly, a solution of compound of Formula III in polar organic solvent is mixed with a solution containing base, catalyst and polar organic solvent. The methylating agent is then added to this mixture. The reaction is usually allowed to proceed for at least 2 hours at −20 to 0° C., and preferably for 2.5-5 hours at −18 to −3° C., most preferably for 3-4 hours at −15 to −5° C. Also, the reaction may be performed at higher or lower temperatures such as any temperature between −20 and 0° C. if the reaction time is adapted accordingly. The O-methylated compound of Formula IV is then isolated from the mixture and purified with non-polar solvent.

Methyl iodide can be used as the methylating agent, sodium hydride or potassium hydroxide as the base, imidazole as the catalyst and THF or DMSO as the solvent for the O-methylation purpose. Non-polar solvent may be used for the purification of the O-methylated compound of Formula IV. Preferably, non-polar solvents, e.g., hexane, heptane, ethers, like petroleum ether, diethyl ether, di-isopropyl ether etc. can be used for the purification purpose.

In another embodiment of this aspect, the O-methylated compound of Formula IV can be optionally subjected to a benzylamination reaction (step-b). The benzylaminating agent used for this purpose is benzylamine ($C_6H_5CH_2NH_2$). The carbonyl moiety present in the compound of Formula IV forms an amide group with the —$NH_2$ moiety of benzylamine in this reaction. The reaction can be performed with benzylamine optionally in a mixed-anhydride condition. The mixed-anhydride coupling reaction conditions are described by, for example, Anderson, et. al. *JACS* (1967), 89, 5012-5017, the contents of which are incorporated herein by reference. The carbonyl group present in Formula IV needs activation before the benzylamination reaction. Some of the examples of compounds that can act as an activator of the carbonyl group are optionally substituted alkyl or aryl chloroformates such as methyl chloroformate, isobutyl chloroformate (IBCF), phenyl chloroformate, nitro-phenyl chloroformate, etc.; azoles such as 1-hydroxybenzotriazole (HOBT) and the like; or imides such as 1,3-dicyclohexylcarbodi-imide (DCC), 1-ethyl-3-(3-dimethylaminopropyl)carbodiimide (EDC) and the like. The benzylamination reaction can be performed in presence of a base. The base selected for the purpose is generally a nitrogen-containing base. Some examples of suitable bases are morpholine, N-methyl morpholine (NMM), triethylamine, diethylamine, isopropylamine (IPA) etc. The solvent used for benzylamination reaction can be an organic solvent. The organic solvent can be, for example, an aliphatic, alicyclic or aromatic solvent. Some examples of solvent are dichloromethane, trichloromethane, tetrachloromethane, ethyl acetate, toluene, tetrahydrofuran (THF), oxirane, acetone and the like.

Accordingly, the base and solution of the activator compound in organic solvent are mixed with a solution of compound of Formula IV in organic solvent, sequentially. The benzylaminating agent is then added to the mixture. The reaction is usually allowed to proceed for at least 1 hour at −20 to 40° C. and preferably for 1.5 hours at −18 to 35° C., most preferably for 2-3 hours at −15 to 30° C. Also, the reaction may be performed at higher or lower temperatures such as any temperature between −20 and 40° C. if the reaction time is adapted accordingly. The benzylaminated compound of Formula V is then isolated and/or purified with non-polar solvent.

Typically, benzylamine as benzylaminating agent, isobutyl chloroformate (IBCF) as an activator of carbonyl group, N-methyl morpholine (NMM) as base and tetrahydrofuran (THF) or ethyl acetate as solvent are used for the benzylamination. Non-polar solvents may be used for the isolation/purification of benzylaminated compound of Formula V. Non-polar solvents such as hexane, heptane, ether like petroleum ether, diethyl ether, di-isopropyl ether etc. can be used for the isolation/purification.

In another embodiment of this aspect, the O-methylated and benzylaminated compound of Formula V is then subjected to de-tritylation reaction (step-c). The de-tritylation can be performed using de-tritylating agents like acids. Strong as well as mild acidic conditions can be suitable for the de-tritylation reaction. Mild acids e.g., acetic acid, etc. or strong acids e.g., hydrochloric acid, sulphuric acid, trifluoroacetic acid etc. can be used. Organic solvents (aromatic or aliphatic) can be used during the reaction. Aromatic solvents e.g., toluene, xylene etc., and aliphatic solvents like chlorinated solvents e.g., dichloromethane, chloroform etc.; alcohols e.g., methanol, ethanol, isopropanol etc. can be used for the de-tritylation purpose. Basic compounds can be used to neutralize the reaction medium. A solution of strong or mild basic compounds is suitable for neutralization. Some examples of these basic compounds are ammonia, ammonium hydroxide, ammonium carbonate, ammonium bicarbonate sodium bicarbonate, sodium carbonate, sodium hydroxide, potassium bicarbonate, potassium carbonate, potassium hydroxide, calcium bicarbonate, calcium hydroxide, calcium carbonate, magnesium hydroxide, magnesium carbonate, magnesium bicarbonate, etc.

Accordingly, the acid is added to the solution of compound of Formula V in organic solvent and the de-tritylation reaction is allowed to proceed for about 1 hour at 15 to 40° C., preferably for 20-50 minutes at 20-35° C., most preferably for 30-40 minutes at 25-30° C. Also, the reaction may be performed at higher or lower temperatures such as any temperature between 15 and 40° C. if the reaction time is adapted accordingly. After completion of the reaction, a solution of the base compound is added to the reaction mixture. The de-tritylated compound of Formula VI is then isolated from the reaction mixture and optionally purified.

Hydrochloric acid or acetic acid as de-tritylating agent, dichloromethane or ethanol as organic solvent and aqueous ammonia solution as base can be used for neutralization. The de-tritylated compound of Formula VI is isolated and optionally purified using organic solvents e.g., dichloromethane, toluene, ethanol, etc.

In another embodiment of present aspect, the de-tritylated compound of Formula VI can be acetylated to produce the compound of Formula I (step-d). For this purpose, acetic anhydride, acetyl chloride, acetic acid or the like and derivatives thereof may be used as an acetylating agent. The acetylation can be performed in the presence or absence of a base. The base can be a nitrogen-containing base e.g., pyridine, dimethylaminopyridine etc. The acetylation reaction can be performed in presence of organic solvents e.g., dichloromethane, toluene, ethyl acetate, etc.

Accordingly, base is added to the solution of compound of Formula VI in organic solvent and acetylating agent is then slowly added to the mixture. The reaction is allowed to proceed for up to 2 hours at temperature ranging from 5 to 40° C. The compound of Formula I is then isolated from the reaction mixture and purified.

Acetic anhydride as acetylating agent, dichloromethane or ethyl acetate as organic solvent and dimethylaminopyridine as base can be used for the acetylation. The compound of Formula I, so formed, is purified with the help of suitable organic solvents such as dichloromethane, toluene, ethanol, ethyl acetate, etc.

The compound of Formula III of present aspect can be prepared by reacting the corresponding serine compound with trityl chloride. The hydroxy and/or carboxylic group of the corresponding serine compound can be protected by a silyl protecting group like, for example, trimethylsilyl, hexamethyldisilazane, etc. and then the free amino group in the compound can be selectively tritylated. Subsequently, the silyl protecting group can be removed by hydrolysis reaction, providing high yields of the compound of Formula III.

In another embodiment of present aspect, a racemic serine compound may be utilized as the starting material. Following the procedure outlined herein would provide the racemic mixture, which can be resolved into the R or S enantiomer by standard techniques known in the art.

In a further embodiment of present aspect, the process outlined herein starting from serine compound in its racemic, R or S enantiomeric form provides the final compound of Formula I in corresponding racemic, R or S form, respectively. If necessary, the optical purity of the product may be enhanced by further separation of the S-enantiomer from the R-enantiomer, by standard techniques known in the art. D-serine (i.e., R-enantiomer) derivatives or L-serine (i.e., S-enantiomer) derivatives or mixtures of D- and L-serine derivatives in any ratio may be used in the method of the present aspect.

A third aspect of the present invention provides a process for the preparation of lacosamide comprising:

O-methylating the compound of Formula IIIa

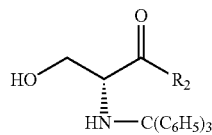

Formula IIIa to produce the compound of Formula IVa

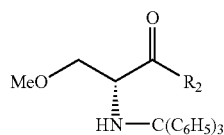

Formula IVa wherein $R_2$ is —OH or —NH—$CH_2$—$C_6H_5$.

The O-methylation method, reagents (e.g., methylating agent, base, catalyst etc.), solvents, process conditions (e.g., temperature, reaction time, etc.) and purification methods are already described herein above for the conversion of the compound of Formula III to give the compound of Formula IV can also be applied in this aspect for the O-methylation of the compound of Formula IIIa to give the compound of Formula IVa.

The optional benzylamination reaction of the compound of Formula IVa, subsequent de-tritylation and $N^2$-acetylation of the compound can afford lacosamide.

In an embodiment of this aspect, racemization is avoided during the process of the present aspect.

In an embodiment of this aspect, the lacosamide obtained by following the process of this aspect is substantially chirally pure. The substantial chiral purity refers to the purity in which no detectable amount of corresponding S-enantiomer is present in lacosamide.

In another embodiment of this aspect, lacosamide prepared by following the process of this aspect is substantially free of impurities. Lacosamide having at least about 99% purity, preferably at least about 99.8% purity and most preferably at least about 99.9% purity can be obtained by the process of present aspect.

In a fourth aspect, a process for the preparation of lacosamide is provided comprising the steps of:

a) O-methylating the compound of Formula VII

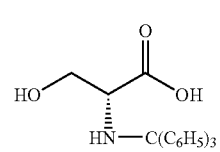

Formula VII to produce a compound of Formula VIII;

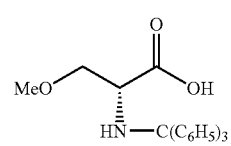

Formula VIII b) benzylaminating the compound of Formula VIII to produce a compound of Formula Va;

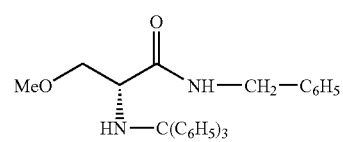

Formula Va c) de-tritylating the compound of Formula Va to produce a compound of Formula VIa; and

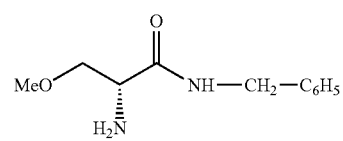

Formula VIa d) acetylating the compound of Formula VIa to produce a compound of Formula Ia.

The O-methylation, benzylamination, de-tritylation, acetylation steps (with respect to method, reaction agents, solvents, catalyst, bases, etc.) and process conditions (e.g., temperature, reaction time, etc.) are described herein for the preparation of 2-acetamido-N-benzyl-3-methoxypropionamide of Formula I can also be applied in this aspect, but for the preparation of lacosamide comprising the steps of this aspect.

In an embodiment of this aspect, racemization is avoided during the process of the present aspect.

In another embodiment of this aspect, the lacosamide obtained by following the process of this aspect is substantially chirally pure. The substantial chiral purity refers to the purity in which no detectable amount of corresponding S-enantiomer is present in lacosamide.

In another embodiment of this aspect, lacosamide prepared by following the process of this aspect is substantially free of impurities. Lacosamide having at least about 99% purity, preferably at least about 99.8% purity and most preferably at least about 99.9% purity can be obtained by the process of present aspect.

In a fifth aspect, a process for the preparation of lacosamide is provided comprising the steps of:

a) benzylaminating the compound of Formula VII

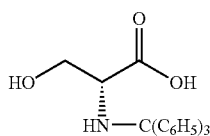

Formula VII to produce a compound of Formula IX;

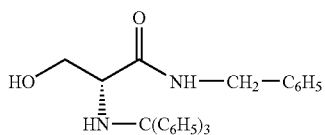

Formula IX b) O-methylating the compound of Formula IX to produce a compound of Formula Va;

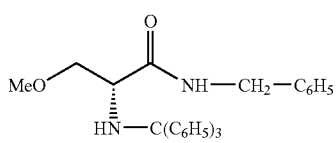

Formula Va c) de-tritylating the compound of Formula Va to produce a compound of Formula VIa; and

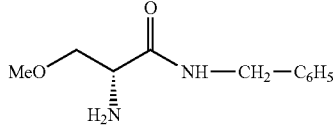

Formula VIa d) acetylating the compound of Formula VIa to produce a compound of Formula Ia.

The O-methylation, benzylamination, de-tritylation, acetylation steps (with respect to method, reaction agents, solvents, catalyst, bases etc.) and process conditions (e.g., temperature, reaction time, etc.) are described herein for the preparation of 2-acetamido-N-benzyl-3-methoxypropiona-mide of Formula I can also be applied in this aspect, but for the preparation of lacosamide comprising the steps of this aspect.

In an embodiment of this aspect, racemization is avoided during the process.

In another embodiment of this aspect, the lacosamide obtained by following the process of this aspect is substantially chirally pure. The substantial chiral purity refers to the purity in which no detectable amount of corresponding S-enantiomer is present in lacosamide.

In another embodiment of this aspect, lacosamide prepared by following the process of this aspect is substantially free of impurities. lacosamide having at least about 99% purity, preferably at least about 99.8% purity and most preferably at least about 99.9% purity can be obtained by the process of present aspect.

In a sixth aspect, substantially chirally pure lacosamide is provided.

In an embodiment of this aspect, lacosamide having chiral purity of more than about 99.8% is preferred. More preferably, lacosamide having chiral purity of at least about 99.9% and most preferably lacosamide having no detectable amount of corresponding S-enantiomer (i.e., 100% chiral purity) is an object of this aspect.

In a seventh aspect, a composition comprising a pharmaceutically effective amount of substantially chirally pure lacosamide along with pharmaceutically acceptable carrier, diluent and/or excipient is provided.

While the present invention has been described in terms of its specific aspects, certain modifications and equivalents will be apparent to those skilled in the art and are intended to be included within the scope of the present invention.

In the following section aspects are described by way of examples to illustrate the processes of the invention. However, these do not limit the scope of the present invention. Several variants of these examples would be evident to persons ordinarily skilled in the art.

EXAMPLE 1

Preparation of N-trityl-D-serine

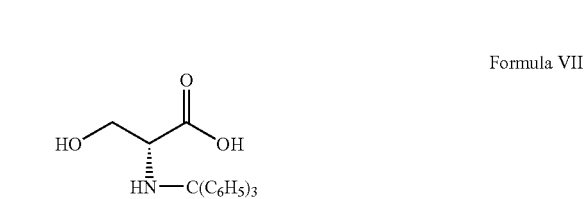

Formula VII

Example 1a

Preparation of N-trityl-D-serine

To dichloromethane (500 ml), D-serine (50 g) was added at ambient temperature under nitrogen atmosphere to form a suspension and then trimethylsilyl chloride (180.91 g) was added to the suspension in 10-15 minutes at ambient temperature. The reaction mixture was refluxed at 35-40° C. for 20 minutes and then it was cooled to ambient temperature. To the reaction mixture, a solution of triethyl amine (168.50 g) in dichloromethane (50 ml) was added in 30-45 minutes at 25-30° C. The mixture was refluxed for 45 minutes at 35-40° C. and then cooled to 0° C. To this mixture, a solution of anhydrous methanol (22.83 g) in dichloromethane (50 ml) was added at 0° C. and the mixture was allowed to reach at room temperature. Triethylamine (48.14 g) was slowly added to it at 25-30° C. and then trityl chloride (132.63 g) was added in 3 lots to the mixture at an interval of 10 minutes. The reaction mixture was then stirred for 3 hours under nitrogen at ambient temperature. After completion of the reaction, methanol (76.12 g) was added at ambient temperature in 10-15 minutes and the solvent was recovered under vacuum at 40-45° C. The crude product obtained was washed with water (750 ml) and filtered. The filtered product was further washed with 5% citric acid solution (750 ml) and filtered. The solid product obtained was partitioned between water (750 ml) and hexanes (200 ml) and then filtered. The filtered solid was washed with hexanes (200 ml) and dried to obtain the titled product. Yield=135 gm.

Example 1b

Preparation of N-trityl-D-serine

To dichloromethane (400 ml), D-serine (50 g) was added at ambient temperature under nitrogen atmosphere to form a suspension and then trimethylsilyl chloride (61.92 g) and hexamethyldisilazane (107.5 ml) was added to the suspension in 10-15 minutes at ambient temperature. The reaction mixture was refluxed at 35-40° C. for 3 hours and then it was cooled to 0° C. To this mixture, a solution of anhydrous methanol (22.83 g) in dichloromethane (50 ml) was added at 0° C. and the mixture was allowed to reach at room temperature. Triethylamine (48.14 g) was slowly added to it at 25-30° C. and then trityl chloride (132.63 g) was added in 3 lots to the mixture at an interval of 10 minutes. The reaction mixture was then stirred for overnight under nitrogen at ambient temperature. After completion of the reaction, methanol (76.12 g) was added at ambient temperature in 10-15 minutes and the solvent was recovered under vacuum at 40-45° C. Hexane (400 ml) and 5% citric acid solution (750 ml) was added to the recovered solid and filtered. The solid product obtained was washed with water (750 ml) and hexanes (200 ml) and then filtered. The filtered solid was washed with hexanes (200 ml) and dried to obtain the titled product. Yield=125 gm.

Example 1c

Preparation of N-trityl-D-serine

To dichloromethane (400 ml), D-serine (50 g) was added at ambient temperature under nitrogen atmosphere to form a suspension and then hexamethyldisilazane (134.15 ml) was added to the suspension in 10-15 minutes at ambient temperature. Catalytic amount of ammonium chloride (1 gm) was added. The reaction mixture was refluxed at 35-40° C. for 3 hours and then it was cooled to 0° C. To this mixture, a solution of anhydrous methanol (22.83 g) in dichloromethane (50 ml) was added at 0° C. and the mixture was allowed to reach at room temperature. Triethylamine (48.14 g) was slowly added to it at 25-30° C. and then trityl chloride (132.63 g) was added in 3 lots to the mixture at an interval of 10 minutes. The reaction mixture was then stirred for overnight under nitrogen at ambient temperature. After completion of the reaction, methanol (76.12 g) was added at ambient temperature in 10-15 minutes and the solvent was recovered under vacuum at 40-45° C. Toluene (400 ml) and 5% citric acid solution (750 ml) was added to the recovered solid and filtered. The solid product obtained was washed with water (750 ml) and hexanes (200 ml) and then filtered. The filtered solid was washed with toluene (200 ml) and dried to obtain the titled product. Yield=100 gm; Mass: (-EI): 346 (M-1); 242.9 (-Tr).

Example 2

Preparation of O-methyl-N-trityl-D-serine

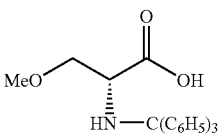

Formula VIII

To a mixture of sodium hydride (20.14 g), imidazole (1.959 g) and tetrahydrofuran (150 ml), a solution of Example 1 product (i.e., N-trityl-D-serine, 50 g) in tetrahydrofuran (500 ml) was added and the mixture was stirred for 45 minutes at −15° C. Methyl iodide (40.8 g) was added to the mixture in 15 minutes at −15° C. to −5° C. and the reaction mixture was stirred at −5° C. for 3 hours. The temperature was raised to 0° C., water was added to it and then the tetrahydrofuran was recovered completely under vacuum at 40° C. Hexane (250 ml) was added to it and stirred for 15 minutes. The layers were separated and the aqueous layer was neutralized with acetic acid till pH=6.0. Dichloromethane (2×150 ml) was added to the aqueous layer and extracted. Organic layer was separated and solvent recovered under vacuum at 35-40° C. to obtain an oily residue. Hexane (100 ml) was added to the oily residue and the solution was stirred for 15 minutes. The product formed was isolated and dried to obtain compound of Formula VIII. Yield=40 gm.

Spectroscopic Data of O-methyl-N-trityl-D-serine $[\alpha]_D^{23}$=+13.9 (c=1, EtOH)

$^1$H NMR (CDCl$_3$) δ: 7.42-7.25, (m, 15 Ph); 6.48 (Br s, NH, OH); 3.4-3.5 (m, CH$_2$—OCH$_3$); 3.1 (s, OCH$_3$) 2.36-2.41 (m-CH—NH)

Mass: 369.9 (M−1);

IR (KBr): 3300, 3294, 2927, 2826, 1655, 1527, 1455, 1360, 1251, 1181, 1106, 971, 734 cm$^{-1}$

Example 3

Preparation of N-benzyl-O-methyl-N$^2$-trityl-D-serinamide

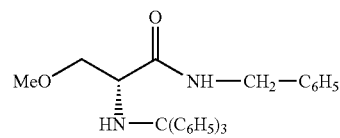

Formula Va

Example 3a

Preparation of N-benzyl-O-methyl-N$^2$-trityl-D-serinamide

To a solution of Example 2 product (i.e., O-methyl-N-trityl-D-serine, 50 g) in tetrahydrofuran (500 ml), N-methyl morpholine (20.9 g) was added at −15° C. in 5-10 minutes. The reaction mixture was stirred for 15 minutes and then isobutylchloroformate (18.8 g) diluted with tetrahydrofuran was added to it at −15° C. under nitrogen atmosphere in 15-20 minutes. The solution was stirred for 15 minutes and benzyl amine (14.7 g) was added to it at −15° C. in 15 minutes. The solution was allowed to cool to room temperature and stirred for 2 hours. The solvent was recovered from the solution. Dichloromethane (250 ml) was added to the crude product and stirred for 5 minutes to dissolve. The dichloromethane layer was washed or stirred for 5 minutes with water (250 ml). The layers were separated and the dichloromethane layer was again washed with 5% NaHCO$_3$ (250 ml). The layers were separated and then the dichloromethane layer was sequentially washed with 5% citric acid solution (250 ml) and then with water (250 ml). The solvent was recovered at 40-45° C. to get oil. Ethyl acetate was added to the oil and the mixture was heated to 60-65° C. to dissolve. The clear solution so formed was cooled upto room temperature and then hexanes (350 ml) were added to it. It was stirred for 1 hour at room temperature, filtered and then dried to get compound of Formula Va. Yield=30 gm.

Example 3b

Preparation of N-benzyl-O-methyl-N$^2$-trityl-D-serinamide

To a solution of Example 2 product (i.e., O-methyl-N-trityl-D-serine, 50 g) in ethyl acetate (500 ml), N-methyl morpholine (20.9 g) was added at −15° C. in 5-10 minutes. The reaction mixture was stirred for 15 minutes and then isobutylchloroformate (18.8 g) already diluted with tetrahydrofuran was added to it at −15° C. under nitrogen atmosphere in 15-20 minutes. The solution was stirred for 15 minutes and benzyl amine (14.7 g) was added to it at −15° C. in 15 minutes. The solution was allowed to cool to room temperature and stirred for 2 hours. The solvent was recovered from the solution. Dichloromethane (250 ml) was added to the crude product and stirred for 5 minutes to dissolve. The dichloromethane layer was washed or stirred for 5 minutes with water (250 ml). The layers were separated and the dichloromethane layer was again washed with 5% NaHCO$_3$ (250 ml). The layers were separated and then the dichloromethane layer was sequentially washed with 5% citric acid solution (250 ml) and then with water (250 ml). The solvent was recovered at 40-45° C. to get oil. Ethyl acetate was added to the oil and the mixture was heated to 60-65° C. to dissolve. The clear solution so formed was cooled up to room temperature and then hexanes (350 ml) were added to it. It was stirred for 1 hour at room temperature, filtered and then dried to get compound of Formula Va. Yield=31 gm.

Spectroscopic Data of N-benzyl-O-methyl-N$^2$-trityl-D-serinamide $[\alpha]_D^{23}$=+91.7 (c=1, EtOH)

$^1$H NMR: 78 (m, NH) 7.41-7.43 (m, 5 Ph); 7.16-7.36 (m, 15 Ph); 4.3-4.5 (m, CH$_2$—NH); 3.49-3.50 (CHH—OCH$_3$) 3.46-3.47 (m, CHH—OCH$_3$); 3.06 (s, OCH$_3$) 2.01-2.06 (m, CH—NH); IR (KBr): 3294, 3024, 2829, 1622, 1527, 1428, 1370 cm$^{-1}$; Mass: 451 (M+1); 243.3 (Tr).

Example 4

Preparation of N-benzyl-O-methyl-D-serinamide

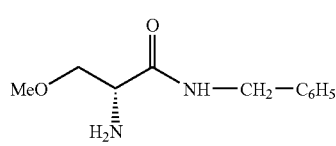

Formula VIa

Example 4a

Preparation of N-benzyl-O-methyl-D-serinamide

To a solution of Example 3 product (i.e. N-benzyl-O-methyl-N$^2$-trityl-D-serinamide, 50 g) in dichloromethane (100 ml), hydrochloric acid (36%) was added at room temperature. This solution was stirred for 30 minutes at room temperature and then the solvent was completely recovered under vacuum at 40° C. Water (250 ml) was added to it at room temperature and the aqueous layer was neutralized with aqueous ammonia (20 ml). The aqueous layer was extracted with toluene (2×200 ml). The toluene was then completely recovered under vacuum at 50-55° C. to get an oil. Yield=15 gm.

Example 4b

Preparation of N-benzyl-O-methyl-D-serinamide

To a solution of Example 3 product (i.e., N-benzyl-O-methyl-N$^2$-trityl-D-serinamide, 50 g) in absolute ethanol (100 ml), acetic acid (1.25 mole eq.) was added at room temperature. This solution was stirred for 30 minutes at room temperature and then the solvent was completely recovered under vacuum at 40° C. Water (250 ml) was added to it at room temperature and the aqueous layer was neutralized with aqueous ammonia (20 ml). The aqueous layer was extracted with toluene (2×200 ml). The toluene was then completely recovered under vacuum at 50-55° C. to get an oil. Yield=18 gm.

Spectroscopic data of N-benzyl-O-methyl-D-serinamide

IR (liq. film): 3352, 3311, 3064, 2964, 2927, 2826, 1655, 1527, 1455, 1360, 1251, 1181, 1106, 971, 734, 700 cm$^{-1}$; $^1$H NMR (CDCl$_3$) δ: 1.85 (br, s, NH$_2$); 3.34 (s, OCH$_3$) 3.56-3.62 (m, CHOCH$_2$), 4.39 (dd, NHCHH), 4.45 (dd, NHCHH); 7.20-7.36 (m, 5 PhH) 7.80-7.88 (m, NH); MS (+CI): 209 (M$^+$+1).

Example 5

Preparation of N-benzyl-N-trityl-D-serinamide

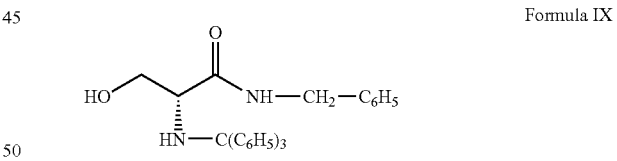

Formula IX

Example 5a

Preparation of N-benzyl-N$^2$-trityl-D-serinamide

N-trityl-D-serine (50 g), prepared by following Example-1, was mixed with tetrahydrofuran (500 ml) and the solution was cooled to −15° C. N-methyl morpholine (15.72 g) was added to it at −15° C. in 5-10 minutes. The solution was stirred for 15 minutes and isobutylchloroformate (20.84 g) diluted with tetrahydrofuran was added to it in 15-20 minutes at −15° C. under nitrogen atmosphere. The solution was stirred for 15 minutes and benzyl amine (18.51 g) was added to it in 15 minutes at −15° C. The solution was further stirred for 45 minutes at −15° C. The solution was allowed to cool to room temperature and stirred for 2 hours. The solvent was recovered from the solution. Dichloromethane (250 ml) was added to the crude product and stirred for 5 minutes to dissolve. The dichloromethane layer was washed or stirred for 5 minutes with water (250 ml). The layers were separated and the dichloromethane layer was again washed with 5% NaHCO$_3$ (250 ml). The layers were separated and then the dichloromethane layer was sequentially washed with 5% citric acid solution (250 ml) and then with water (250 ml). The solvent was recovered at 40-45° C. to get oil. Ethyl acetate (150 ml) was added to the oil and the mixture was heated to 60-65° C. to dissolve. The clear solution so formed was cooled upto room temperature and then hexanes (350 ml) were added to it. It was stirred for 1 hour at room temperature, filtered and then dried to get the compound of Formula IX. Yield=45 gm.

Example 5b

Preparation of N-benzyl-N$^2$-trityl-D-serinamide

N-trityl-D-serine (50 g), prepared by following example-1, was mixed with ethyl acetate (500 ml) and the solution was cooled to −15° C. N-methyl morpholine (15.72 g) was added to it at −15° C. in 5-10 minutes. The solution was stirred for 15 minutes and isobutylchloroformate (20.84 g) diluted with tetrahydrofuran was added to it in 15-20 minutes at −15° C. under nitrogen atmosphere. The solution was stirred for 15 minutes and benzyl amine (18.51 g) was added to it in 15 minutes at −15° C. The solution was further stirred for 45 minutes at −15° C. The solution was allowed to cool to room temperature and stirred for 2 hours. The solvent was recovered from the solution. Dichloromethane (250 ml) was added to the crude product and stirred for 5 minutes to dissolve. The dichloromethane layer was washed or stirred for 5 minutes with water (250 ml). The layers were separated and the dichloromethane layer was again washed with 5% NaHCO$_3$ (250 ml). The layers were separated and then the dichloromethane layer was sequentially washed with 5% citric acid solution (250 ml) and then with water (250 ml). The solvent was recovered at 40-45° C. to get oil. Ethyl acetate (150 ml) was added to the oil and the mixture was heated to 60-65° C. to dissolve. The clear solution so formed was cooled upto room temperature and then hexanes (350 ml) were added to it. It was stirred for 1 hour at room temperature, filtered and then dried to get the compound of Formula IX. Yield=45.5 gm.

Example 6

Preparation of N-benzyl-O-methyl-N$^2$-trityl-D-serinamide

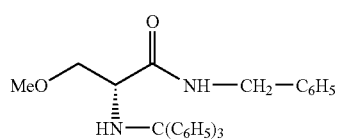

Formula Va

Example 6a

Preparation of N-benzyl-O-methyl-N$^2$-trityl-D-serinamide

To a mixture of sodium hydride (6.59 g), imidazole (1.564 g) and tetrahydrofuran (150 ml), a solution of Example 5 product (i.e. N-benzyl-N$^2$-trityl-D-serinamide, 50 g) in tetrahydrofuran (500 ml) was slowly added at −15° C. and the mixture was stirred for 45 minutes at −15° C. Methyl iodide (24.38 g) was slowly added to the mixture for 15 minutes at −15° C. to −5° C. and the formed reaction mixture was stirred at −5° C. for 3 hours. The reaction mixture was cooled to 0° C., water was added to it and then the tetrahydrofuran was recovered completely under vacuum at 40° C. Hexane (250 ml) was added to it and stirred for 15 minutes. The layers were separated and the aqueous layer was neutralized with acetic acid till pH=6.0. Dichloromethane (2×150 ml) was added to the aqueous layer and layers were separated. Oily product was recovered under vacuum at 35-40° C. from the organic layer. Hexane (100 ml) was added to the oily product and the solution formed is stirred for 15 minutes, filtered and dried to get the titled product of Formula Va.
Yield=30 gm.

Example 6b

Preparation of N-benzyl-O-methyl-N$^2$-trityl-D-serinamide

To a mixture of DMSO (8 g) and pulverized KOH (0.308 g), Example 5 product (i.e., N-benzyl-N$^2$-trityl-D-serinamide, 2 g) was added in one lot. It was stirred for 3 hours at ambient temperature. Methyl iodide (0.97 g) was slowly added to the mixture for 15 minutes at ambient temperature and stirred for 30 minutes. The reaction mixture was cooled to 0° C., water was added to it and the product was isolated with toluene. Oily product was recovered under vacuum at 35-40° C. from the organic layer. Hexane (100 ml) was added to the oily product and the solution formed is stirred for 15 minutes, filtered and dried to get the titled product of Formula Va.
Yield=1 gm.
Spectroscopic Data of N-benzyl-O-methyl-N$^2$-trityl-D-serinamide
$[\alpha]_D^{23}$=+91.7 (c=1, EtOH)
$^1$H NMR: 78 (m, NH) 7.41-7.43 (m, 5 Ph); 7.16-7.36 (m, 15 Ph); 4.3-4.5 (m, CH$_2$—NH); 3.49-3.50 (CHH—OCH$_3$) 3.46-3.47 (m, CHH—OCH$_3$); 3.06 (s, OCH$_3$) 2.01-2.06 (m, CH—NH); IR (KBr): 3294, 3024, 2829, 1622, 1527, 1428, 1370 cm$^{-1}$; Mass: 451 (M+1); 243.3 (Tr).

Example 7

Preparation of Lacosamide

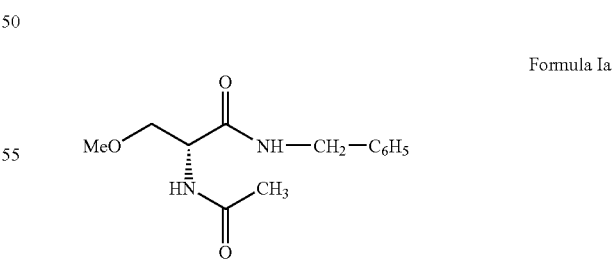

Formula Ia

Example 7a

Preparation of Lacosamide

N-benzyl-O-methyl-D-serinamide (50 g), prepared by sequentially following Example 1 to Example 4, was mixed with dichloromethane (500 ml) at ambient temperature and stirred to get clear solution. To this solution, dimethylaminopyridine (1.04 g) was added at ambient temperature. The solution was cooled to 10° to 5° C. and then acetic anhydride (24.48 g) was slowly added to it for 10-15 minutes at 10° to 5° C. The solution was stirred for 10 minutes at 10° to 5° C. and raised to room temperature (25°-30° C.) in over 30 minutes. The solution was further stirred for 30 minutes at room temperature. The reaction mixture was washed with 8% sodium bicarbonate (250 ml) solution. It was again washed with water (250 ml). The layers were separated and solvent was completely recovered under vacuum at 40-48° C. to get a solid product. Yield=50 gm; mp: 142-143° C. Chiral purity of lacosamide by HPLC, 99.98%.

Example 7b

Preparation of Lacosamide

N-benzyl-O-methyl-D-serinamide (50 g), prepared by sequentially following Example-1 to Example 4, was mixed with ethyl acetate (500 ml) at ambient temperature and stirred to get clear solution. To this solution, dimethylaminopyridine (1.04 g) was added at ambient temperature. The solution was cooled to 10° to 5° C. and then acetic anhydride (24.48 g) was slowly added to it for 10-15 minutes at 10° to 5° C. The solution was stirred for 10 minutes at 10° to 5° C. and raised to room temperature (25°-30° C.) in over 30 minutes. The solution was further stirred for 30 minutes room temperature. The reaction mixture was washed with 8% sodium bicarbonate (250 ml) solution. It was again washed with water (250 ml). The layers were separated and solvent was completely recovered under vacuum at 40-48° C. to get a solid product. Yield=49.5 gm; mp: 142-143° C. Chiral purity of lacosamide by HPLC, 99.98%.

Example 8

Preparation of Lacosamide

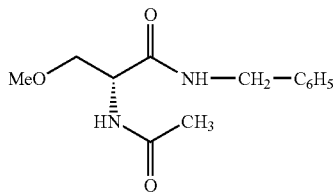

Formula Ia

Example 8a

Preparation of Lacosamide

N-benzyl-O-methyl-D-serinamide (50 g), prepared by sequentially following Example 1, 5, 6 and 4, was mixed with dichloromethane (500 ml) at ambient temperature and stirred to get clear solution. To this solution, dimethylaminopyridine (1.04 g) was added at ambient temperature. The solution was cooled to 10° to 5° C. and then acetic anhydride (24.48 g) was slowly added to it for 10-15 minutes at 10° to 5° C. The solution was stirred for 10 minutes at 10° to 5° C. and raised to room temperature (25°-30° C.) in over 30 minutes. The solution was further stirred for 30 minutes at room temperature. The reaction mixture was washed with 8% sodium bicarbonate (250 ml) solution. It was again washed with water (250 ml). The layers were separated and solvent was completely recovered under vacuum at 40-48° C. to get solid product. Yield=49 gm; mp: 142-143° C. Chiral purity of lacosamide by HPLC, 99.98%.

Example 8b

Preparation of Lacosamide

N-benzyl-O-methyl-D-serinamide (50 g), prepared by sequentially following Example 1, 5, 6 and 4, was mixed with ethyl acetate (500 ml) at ambient temperature and stirred to get clear solution. To this solution, dimethylaminopyridine (1.04 g) was added at ambient temperature. The solution was cooled to 10° to 5° C. and then acetic anhydride (24.48 g) was slowly added to it for 10-15 minutes at 10° to 5° C. The solution was stirred for 10 minutes at 10° to 5° C. and raised to room temperature (25°-30° C.) in over 30 minutes. The solution was further stirred for 30 minutes at room temperature. The reaction mixture was washed with 8% sodium bicarbonate (250 ml) solution. It was again washed with water (250 ml). The layers were separated and solvent was completely recovered under vacuum at 40-48° C. to get solid product. Yield=49.5 gm; mp: 142-143° C. Chiral purity of lacosamide by HPLC, 99.98%.

Example 9

Preparation of Lacosamide

N-benzyl-O-methyl-D-serinamide (92 g), was mixed with dichloromethane (368 ml) at ambient temperature and stirred for 10 minutes to get a clear solution. To this solution, dimethylaminopyridine (0.47 g) was added at ambient temperature. Acetic anhydride (45.09 g) was slowly added over 15-20 minutes at ambient temperature. The solution was stirred for 2 hours at room temperature. The reaction mixture was washed with sodium hydroxide (19.16 gm dissolved in 291 ml water), and deionized water (276 ml). The layers were separated and solvent was completely recovered under vacuum at 35-40° C. to get crude product. Yield=82.6 gm; Chiral purity=100%.

5 gm of the crude product was dissolved in toluene (35 ml) and heated to 80° C. It was then cooled to room temperature and stirred for 30 minutes. The material was cooled further to 0° C. and stirred for 30 minutes at the same temperature. The mixture was filtered, and washed with chilled toluene (2×10 ml). The filtrate was suck-dried for 15 minutes and dried under vacuum at 45-50° C. Dried wt=4.5 gm; Chiral purity of lacosamide by HPLC, 100.00%.

Example 10

Preparation of Lacosamide

N-benzyl-O-methyl-D-serinamide (5 g), was mixed with DCM (25 ml) at ambient temperature and stirred for 10 minutes to get a clear solution. To this solution, dimethylaminopyridine (0.025 g) was added at ambient temperature. Acetic anhydride (2.695 g) was slowly added over 10-12 minutes at ambient temperature. The solution was stirred for 30 minutes at room temperature. The reaction mixture was washed with 5% sodium bicarbonate (15 ml) solution, deionized water (15 ml), and brine (10 ml). The layers were separated and solvent was completely recovered under vacuum at 35-40° C. to get crude product. Yield=5.9 gm.

1 gm of the crude product was dissolved in ethyl acetate (6 ml) and heated to reflux to get a clear solution. The mixture was cooled to room temperature in 1 hour, cooled further to 5° C. in 15 minutes, then stirred for 1 hour at 5-10° C. The solid was filtered, and washed with chilled ethyl acetate (3.0 ml). The material was suck-dried for 15 minutes, and finally dried under vacuum at 50-55° C. Dried wt=0.5 g. Chiral purity of lacosamide by HPLC, 100.00%.

We claim:

1. A process for the preparation of lacosamide comprising the steps of:

a) O-methylating the compound of Formula VII

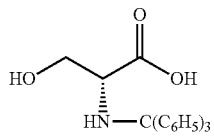

Formula VII to produce a compound of Formula VIII:

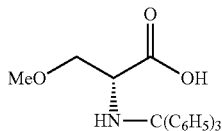

Formula VIII b) benzylaminating the compound of Formula VIII to produce a compound of Formula Va;

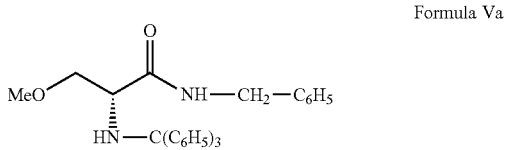

Formula Va c) de-tritylating the compound of Formula Va to produce a compound of Formula VIa; and

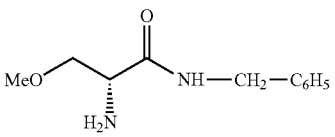

Formula VIa d) acetylating the compound of Formula VIa to produce lacosamide.

* * * * *